United States Patent [19]

Müller et al.

[11] Patent Number: 5,508,299

[45] Date of Patent: Apr. 16, 1996

[54] IMIDAZOLYL-SUBSTITUTED CYCLOHEXANE DERIVATIVES

[75] Inventors: Ulrich E. Müller; Jürgen Dressel;
Peter Fey, all of Wuppertal; Rudolf H. Hanko, Duesseldorf; Walter Hübsch; Thomas Krämer, both of Wuppertal; Matthias Müller-Gliemann, Solingen; Martin Beuck, Erkrath; Stanislav Kazda, Wuppertal; Andreas Knorr, Erkrath; Johannes-Peter Stasch, Wuppertal; Stefan Wohlfeil, Hilden, all of Germany

[73] Assignee: Bayer Aktiengesellschaft, Leverkusen, Germany

[21] Appl. No.: 80,853

[22] Filed: Jun. 21, 1993

[30] Foreign Application Priority Data

Jun. 26, 1992 [DE] Germany .................. 42 21 009.7

[51] Int. Cl.⁶ .............. A61K 31/415; C07D 233/68; C07D 233/70
[52] U.S. Cl. ............. 514/400; 548/336.1; 548/337.1; 548/338.1; 548/339.5; 548/340.1; 548/341.1; 548/341.5
[58] Field of Search ............ 548/336.1, 337.1, 548/338.1, 339.5, 340.1, 341.1, 341.5; 514/400

[56] References Cited

U.S. PATENT DOCUMENTS 4,355,040  10/1982  Furukawa et al. ............. 424/273 R
5,153,197  10/1992  Carini et al. .................. 514/255
5,254,546  10/1993  Ardecky et al. ............... 514/225.8

FOREIGN PATENT DOCUMENTS 0253310  1/1988  European Pat. Off. .
0324377  7/1989  European Pat. Off. .

OTHER PUBLICATIONS

*Russian Chemical Reviews Uspekhi Khimii*, Jan. 1963, pp. 1–20; R. V. Vizgert "Mechanisms of the Hydrolysis of Aromatic Sulphonyl Chlorides and of . . . ".
*Journal of the American Chemical Society*, 95:3, Feb. 7, 1973, pp. 875–879; J. C. Sheehan et al, "Total Synthesis of a Monocyclic Peptide Lactone . . . ".
*The Journal of Biological Chemistry*, vol. 258, No. 11, Jun. 10, 1983, pp. 7087–7093; F. E. Frerman et al., "Leucine Catabolism During the Differentiation . . . ".
*Int. J. Peptide Protein Res.*, vol. 17, 1981, pp. 197–204; N. L. Benoiton et al., "Studies on Racemization During Couplings Using a Series of . . . ".

*Primary Examiner*—Patricia L. Morris
*Attorney, Agent, or Firm*—Sprung Horn Kramer & Woods

[57] ABSTRACT

Imidazolyl-substituted cyclohexane derivatives are prepared by reacting appropriate cyclohexane derivatives with substituted imidazoles and subsequent variation of the substituents.

The imidazolyl-substituted cyclohexane derivatives can be employed as active compounds in medicaments, in particular for the treatment of arterial hypertension and atherosclerosis.

6 Claims, No Drawings

IMIDAZOLYL-SUBSTITUTED CYCLOHEXANE DERIVATIVES

The invention relates to imidazolyl-substituted cyclohexane derivatives, a process for their preparation and their use in medicaments, in particular as hypotensive and antiatherosclorotic agents.

It is known that renin, a proteolytic enzyme, eliminates the decapeptide angiotensin I in vivo from angiotensinogen, and the angiotensin I is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, cardiac muscle cells and smooth muscle cells, these growing and proliferating at an increased rate in various disease states (for example hypertension, atherosclerosis and cardiac insufficiency).

In addition to the inhibition of renin activity, a possible starting point for intervention in the renin-angiotensin system (RAS) is the inhibition of the activity of angiotensin-converting enzyme (ACE) and the blockade of angiotensin II receptors.

In addition, imidazole derivatives having angiotensin II-inhibiting action are disclosed in WO 91/00-281-A, WO 91/00-277-A, EP 253,303 A, EP 253,310 and EP 324,377.

The present invention relates to imidazolyl-substituted cyclohexane derivatives of the general formula (I)

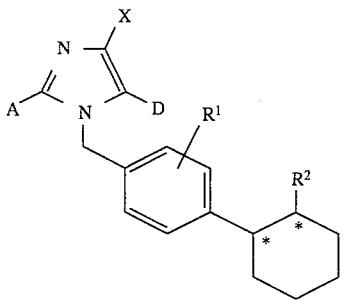

in which

A represents straight-chain or branched alkyl or alkenyl each having up to 8 carbon atoms, or represents cycloalkyl having 3 to 8 carbon atoms, X represents hydrogen, halogen or perfluoroalkyl having up to 5 carbon atoms, X represents a group of the formula $-CH_2-OR^3$ or $-CO-R^4$, in which R$^3$ denotes hydrogen or straight-chain or branched alkyl having up to 8 carbon atoms, R$^4$ denotes hydrogen, hydroxyl or straight-chain or branched alkoxy having up to 8 carbon atoms, R$^1$ represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl, R$^2$ represents a radical of the formula $-CO-R^5$, $-CO-NR^6R^7$ or

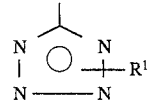

in which

R$^5$ denotes hydroxyl or straight-chain or branched alkoxy having up to 8 carbon atoms, R$^6$ denotes hydrogen or straight-chain or branched alkyl having up to 6 carbon atoms, R$^7$ denotes a radical of the formula $-SO_2R^9$ or

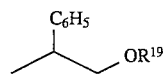

in which

R$^9$ denotes straight-chain or branched alkyl having up to 8 carbon atoms, which is optionally substituted by phenyl or tolyl, or denotes phenyl, which is optionally substituted by halogen or by straight-chain or branched alkyl having up to 6 carbon atoms, R$^{10}$ denotes hydrogen, straight-chain or branched alkyl having up to 6 carbon atoms or a hydroxyl protective group, R$^8$ denotes hydrogen, straight-chain or branched alkyl having up to 4 carbon atoms or the triphenylmethyl group and their salts.

The compounds of the general formula I according to the invention can also be present in the form of their salts. In general, salts with organic or inorganic bases or acids may be mentioned here.

In the context of the present invention, physiologically acceptable salts are preferred. Physiologically acceptable salts of the imidazolyl-substituted cyclohexane derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which behave either as image and mirror image (enantiomers), or which do not behave as image and mirror image (diastereomers). The invention relates both to the enantiomers or diastereomers and to their respective mixtures. Like the diastereomers, the racemic forms can be separated in a known manner into the stereoisomerically uniform constituents [cf. E. L. Eliel, Stereochemistry of Carbon Compounds, McGraw Hill, 1962].

Hydroxyl protective group in the context of the above-mentioned definition in general represents a protective group of the series: trimethylsilyl, triethylsilyl, triisopropylsilyl, tert-butyldimethylsilyl, tert-butyldiphenylsilyl, trimethylsilylethoxycarbonyl, benzyl, triphenylmethyl(trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butoxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethorybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl, or 4-methoxybenzoyl. Acetyl is preferred.

Preferred compounds of the general formula (I) are those in which

A represents straight-chain or branched alkyl or alkenyl each having up to 6 carbon atoms, or represents cyclopropyl, cyclobutyl, cyclopentyl, cyclohexyl or cycloheptyl, X represents hydrogen, fluorine, chlorine, bromine or perfluoroalkyl having up to 4 carbon atoms, D represents a group of the formula —$CH_2OR^3$ or —$CO-R^4$, in which $R^3$ denotes hydrogen or straight-chain or branched alkyl having up to 6 carbon atoms, $R^4$ denotes hydrogen, hydroxyl or straight-chain or branched alkoxy having up to 6 carbon atoms, $R^1$ represents hydrogen, fluorine, chlorine, bromine, trifluoromethyl, carboxyl or straight-chain or branched alkyl, alkoxy or alkoxycarbonyl each having up to 4 carbon atoms, $R^2$ represents a radical of the formula —CO—$R^5$, —CO—$NR^6R^7$

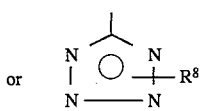

in which $R^5$ denotes hydroxyl or straight-chain or branched alkoxy having up to 6 carbon atoms, $R^6$ denotes hydrogen or straight-chain or branched alkyl having up to 4 carbon atoms, $R^8$ denotes a radical of the formula —$SO_2$—$R^9$ or

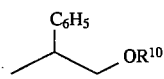

in which $R^9$ denotes straight-chain or branched alkyl having up to 6 carbon atoms, which is optionally substituted by phenyl or tolyl, or denotes phenyl which is optionally substituted by fluorine, chlorine or bromine, or by straight-chain or branched alkyl having up to 4 carbon atoms, $R^{10}$ denotes hydrogen or straight-chain or branched alkyl having up to 4 carbon atoms or benzyl, $R^8$ denotes hydrogen, methyl, ethyl or the triphenylmethyl group, and their salts.

Particularly preferred compounds of the general formula (I) are those in which

A represents straight-chain or branched alkyl or alkenyl each having up to 4 carbon atoms, or represents cyclopropyl, cyclopentyl or cyclohexyl, B represents hydrogen, fluorine, chlorine or perfluoroalkyl having up to 3 carbon atoms, D represents a group of the formula —$CH_2OR^3$ or —$CO-R^4$, in which $R^3$ denotes hydrogen or straight-chain or branched alkyl having up to 4 carbon atoms, $R^4$ denotes hydrogen, hydroxyl or straight-chain or branched alkoxy having up to 4 carbon atoms, $R^1$ represents hydrogen, fluorine, chlorine, bromine, trifluoromethyl or methyl, $R^2$ represents a radical of the formula —CO—$R^5$, —CO—$NR^6R^7$

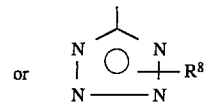

in which $R^5$ denotes hydroxyl or straight-chain or branched alkoxy having up to 4 carbon atoms, $R^6$ denotes hydrogen, methyl or ethyl, $R^7$ denotes a radical of the formula —$SO_2R^9$ or

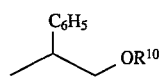

in which $R^9$ denotes straight-chain or branched alkyl having up to 4 carbon atoms, which is optionally substituted by phenyl or tolyl, or denotes phenyl or tolyl, $R^{10}$ denotes hydrogen, methyl or ethyl, $R^8$ denotes hydrogen, methyl or the triphenylmethyl group and their salts.

A process for the preparation of the compounds of the general formula (I) according to the invention has additionally been found, characterised in that cyclohexane compounds of the general formula (II)

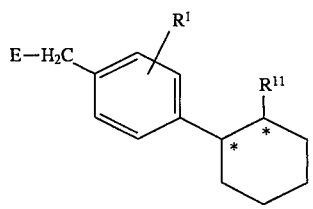

in which

E represents a typical leaving group such as, for example, chlorine, bromine, iodine, tosylate or mesylate, preferably bromine, $R^1$ has the abovementioned meaning and $R^{11}$ denotes straight-chain or branched $C_1$–$C_4$-alkoxycarbonyl or the triphenylmethyl-tetrazol-1-yl group, are reacted first with imidazoles of the general formula (III)

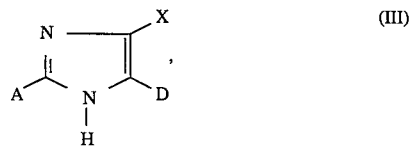

in which

A, B and D have the abovementioned meaning, in inert solvents, if appropriate in the presence of a base and if appropriate under a protective gas atmosphere, to give compounds of the general formula (IV)

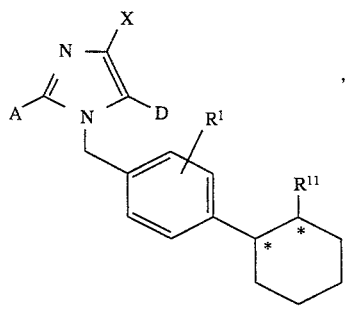

in which

A, B, D, $R^1$ and $R^{11}$ have the abovementioned meaning, in the case of the acids ($R^2=CO_2H$) the esters are hydrolysed, and in the case of the amides and sulphonamides, starting from the corresponding carboxylic acids, the products are amidated in inert solvents, after prior activation with compounds of the general formula (V)

$$H-NR^6R^7 \qquad (V)$$

in which $R^6$ and $R^7$ have the abovementioned meaning, if appropriate in the presence of a base and/or of an auxiliary, for example of a dehydrating agent, and in the case of the free tetrazole, the trityl group is removed using acids, preferably trifluoroacetic acid or hydrochloric acid in dioxane, and if appropriate the substituents A, B, D and $R^1$ are introduced or converted into other groups by customary methods, for example by reduction, oxidation, alkylation or hydrolysis, and if appropriate the isomers are separated, and in the case of the preparation of the salts reacted with an appropriate base or acid.

The process according to the invention can be illustrated by way of example by the following reaction scheme:

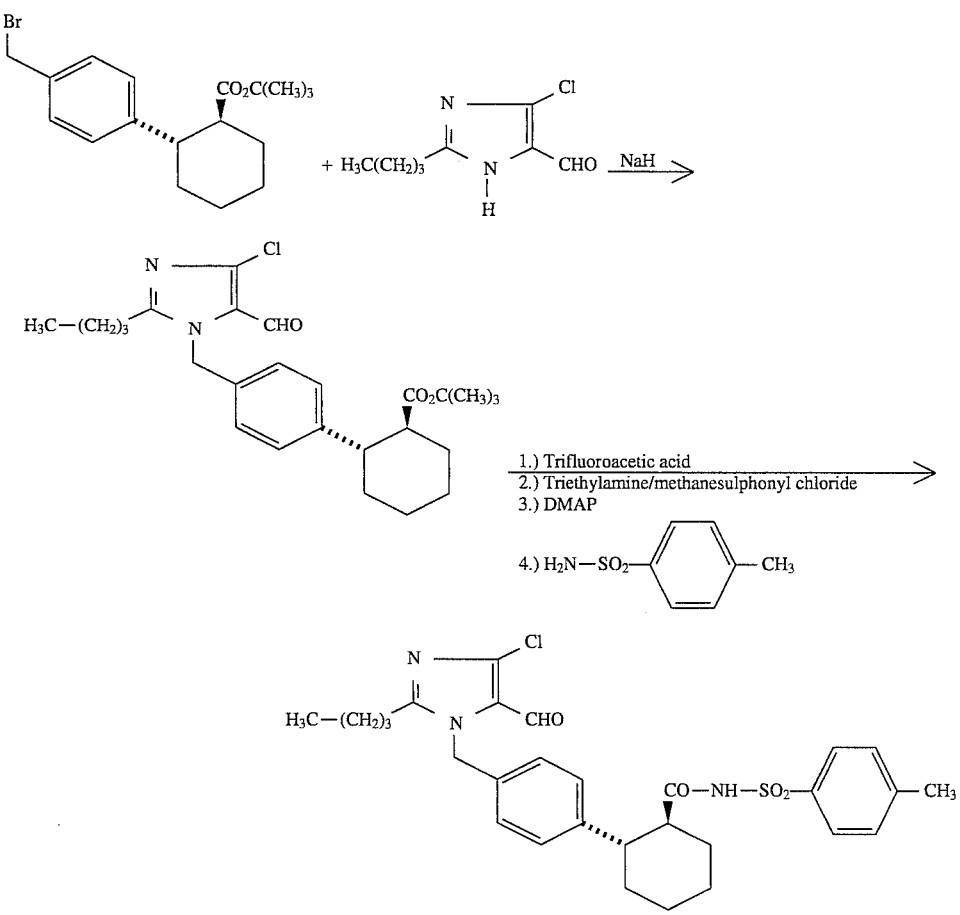

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium or their hydrides such as sodium hydride. Sodium hydride, potassium carbonate, triethylamine, pyridine and potassium tert-butoxide are preferred.

In general, the base is employed in an amount from 0.05 mol to 10 mol, preferably from 1 mol to 2 mol, relative to 1 mol of the compound of the formula (III).

The process according to the invention is in general carried out in a temperature range from –30° C. to +100° C., preferably from –10° C. to +60° C.

The process according to the invention is in general carried out at normal pressure. However, it is also possible to carry out the process at elevated pressure or at reduced pressure (.for example in a range from 0.5 to 5 bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol, butanol or tert-butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis is preferably carried out using acids such as, for example, trifluoroacetic acid, acetic acid, hydrochloric acid, hydrochloric acid in dioxane, hydrobromic acid, methanesulphonic acid, sulphuric acid or perchloric acid. Trifluoroacetic acid or hydrochloric acid in dioxane are particularly preferred.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has proven advantageous in this case in the preparation of the carboxylic acids to acidify the basic reaction mixture from the hydrolysis in a second step without isolation of the carboxylates. The acids can then be isolated in a customary manner.

The amidation and the sulphoamidation starting from the compounds of the general formula (IV) are in general carried out in one of the abovementioned solvents, preferably in tetrahydrofuran or dichloromethane.

The amidation and the sulphoamidation can optionally take place via the activated stage of the acid halides or mixed anhydrides, which can be prepared from the appropriate acids by reaction with thionyl chloride, phosphorus trichloride, phosphorus pentachloride, phosphorus tribromide, oxalyl chloride or methanesulphonyl chloride.

The amidation and the sulphoamidation are in general carried out in a temperature range from –50° C. to +80° C., preferably from –30° C. to +20° C., and at normal pressure.

Suitable bases for this in addition to the abovementioned bases are preferably triethylamine and/or (dimethylamino)pyridine, DBU or DABCO.

The base is employed in an amount from 0.5 mol to 10 mol, preferably from 1 mol to 5 mol, relative to 1 mol of the compound of the general formula (IV).

Acid-binding agents which can be employed for the amidation are alkali metal or alkaline earth metal carbonates such as sodiumcarbonate, potassium carbonate, alkali metal or alkaline earth metal hydroxides such as, for example, sodium hydroxide or potassium hydroxide, or organic bases such as pyridine, triethylamine or N-methylpiperidine, or bicyclic amidines such as 1,5-diazabicyclo[ 3.4.0]-non-5-ene (DBN) or 1,5-diazabicyclo[ 3.4.0]undec-5-ene (DBU). Triethylamine is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. Ledis, J. Am. Chem. Soc. 95, 875 1973); F. E. Freeman et al., J. Biol. Chem. 258, 7087–7093 (1983) and N. B. Benoton, K. Kluroda, Int. Pept. Prot. Res. 17, 197 (1981)].

The acid-binding agents and dehydrating reagents are in general employed in an amount from 0.5 to 3 mol, preferably from 1 to 1.5 mol, relative to 1 mol of the corresponding carboxylic acids.

The abovementioned derivatisation of the substituents A, B, D and $R^1$ is in general carried out according to methods known from the literature, where, for example, the reduction of aldehydes or alkoxycarbonyl compounds to alcohols (a), the oxidation of aldehydes to carboxylic acids (b) and the alkylation (c) will be explained by the following:

a) The reduction of alkoxycarbonyl compounds or aldehydes to the corresponding alcohols is in general carried out using hydrides, such as lithium aluminium hydride or sodium borohydride, preferably using lithium aluminium hydride in inert solvents such as ethers, hydrocarbons or alcohols or mixtures thereof, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C., preferably from +20° C. to +100° C., at normal pressure.

b) The oxidation of aldehydes to the carboxylic acids is in general carried out in one of the abovementioned solvents, preferably tert-butanol, using potassium permanganate, in the presence of sodium hydrogen phosphate and sodium sulphite, in a temperature range from −30° C. to +20° C., preferably from −20° C. to +20° C. and at normal pressure.

c) The alkylation is in general carried out in one of the abovementioned solvents using alkylating agents such as, for example, ($C_1$–$C_8$)-alkyl halides, sulphonic acid esters or substituted or unsubstituted ($C_1$–$C_6$)-dialkyl or ($C_1$–$C_{10}$)-diaryl sulphates, preferably methyl iodide, p-toluenesulphonic acid esters or dimethyl sulphate.

The cyclohexane compounds of the general formula (II) are new and can be prepared by converting compounds of the general formula (VI)

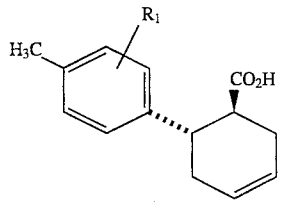
(VI)

in which $R^1$ has the abovementioned meaning, first by hydrogenation with palladium/C in one of the abovementioned solvents, preferably methanol, in a hydrogen atmosphere into the compounds of the general formula (VII)

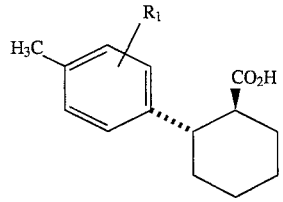
(VII)

in which $R^1$ has the abovementioned meaning, in a second step, if $R^2 \neq$ tetrazolyl, esterifying according to customary methods and, if $R^2$ represents the tetrazolyl radical, reacting with chlorosulphonyl isocyanate in dichloromethane to give the corresponding cyano compounds, then introducing the tetrazolyl group using sodium azide/triethylammonium chloride, in the presence of one of the abovementioned bases, preferably N,N-dimethylformamide, under a nitrogen atmosphere, introducing the triphenylmethyl group by further reaction with triphenylmethyl chloride in the presence of one of the abovementioned solvents and bases, preferably dichloromethane and triethylamine, and in the last step carrying out a bromination of the methylene group, if appropriate in the presence of a catalyst.

The reduction of the double bond is carried out in a temperature range from 0° C. to +40° C., preferably at +20° C. and a pressure of 1 bar.

The esterification is carried out in one of the abovementioned solvents, preferably toluene and tetrahydrofuran, after the prior activation of the corresponding carboxylic acid which was already described above, preferably via the carbonyl chlorides, and subsequent reaction with the corresponding alkoxides, in a temperature range from 0° C. to +60° C., preferably at +10° C. to +35° C. and at normal pressure.

The reactions to give the cyano compounds and the tetrazolyl compounds are in general carried out at the boiling point of the respective solvent and at normal pressure.

The introduction of the triphenylmethyl group into the tetrazolyl ring is in general carried out at 0° C.

The bromination is in general carried out in a temperature range from +40° C. to 100° C., preferably from +60° C. to +90° C. and at normal pressure. It is carried out in one of the abovementioned solvents, preferably using carbon tetrachloride, and using N-bromosuccinimide.

A suitable starter (catalyst) for the bromination is, for example, azobisisobutyronitrile or dibenzoyl peroxide, preferably azobisisobutyronitrile, the starter being employed in an amount from 0.01 mol to 0.1 mol, preferably from 0.01 mol to 0.05 mol, relative to 1 mol of the compound of the general formula (VII).

The compounds of the general formula (VI) are also new and can be prepared, for example, by reacting compounds of the general formula (VIII)

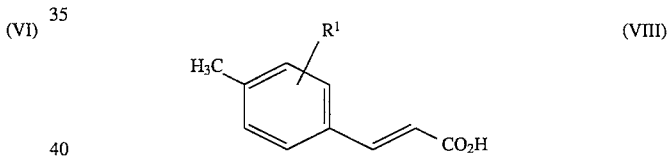
(VIII)

in which $R^1$ has the abovementioned meaning, in one of the abovementioned solvents, preferably toluene, with 1,3-butadiene in the presence of hydroquinone, in a temperature range from +180° C. to +230° C., preferably at 200° C. and a pressure of about 20 bar [cf. Eur. J. Med. Chem. 11, 493 (1976)].

The compounds of the general formula (VIII) are known per se or can be prepared by customary methods [cf. Organikum, VEB Deutscher Verlag der Wissenschaften, Berlin 1977, pages 572 ff.].

The compounds of the general formulae (IV) and (VII) are new and can be prepared, for example, by the processes described above.

The compounds of the general formula (II) are likewise known per se [cf., for example, EP 324,377, Beilstein 25, 163; 23, 45; U.S. Pat. No. 4,355,040] or can be prepared by a customary method.

The amines of the general formula (V) are known or can be prepared by known processes [cf., for example, Beilstein 11/104, R. V. Vitzgert, Uspekhi, Khimii 32, 3 (1963); Russian Chem. Rev. 32, 1 (1963); Beilstein 4, 87].

The compounds of the general formula (I) according to the invention exhibit an unforeseeable, useful spectrum of pharmacological actions.

The compounds according to the invention have a specific A II-antagonistic action, since they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, brain function disorders, ischemic cerebral diseases, peripheral circulatory disorders, functional disorders of the kidney and adrenal gland, bronchospastic diseases and diseases of the respiratory tract having a vascular component, sodium retention and oedemas.

Investigation of the inhibition of the contraction induced by agonists

Rabbits of either sex are stunned by a blow to the back of the head and bled out, or in some cases anaesthetised with Nembutal (about 60–80 mg/kg i.v.) and sacrificed by opening the thorax. The thorax aorta is removed, freed from adhering connective tissue, divided into ring segments 1.5 mm wide and individually transferred under an initial loading of about 3.5 g to 10 ml organ baths containing Krebs-Henseleit nutrient solution, aerated with 95% $O_2$/5% $CO_2$ and temperature-controlled at 37° C., of the following composition: 119 mmol/l of NaCl; 2.5 mmol/l of $CaCl_2 \times 2H_2O$; 1.2 mmol/l of $KH_2PO_4$; 10 mmol/l of glucose; 4.8 mmol/l of KCl; 1.4 mmol/l of $MgSO_4 \times 7 H_2O$ and 25 mmol/l of $NaHCO_3$.

The contractions are determined isometrically by means of Statham UC2 cells via bridge amplifiers (ifd Mülheim or DSM Aalen) and digitalised by means of A/D converters (System 570, Keithley Munich) and assessed. The agonist dose response curves (DRCs) are plotted hourly. With each DRC, 3 or 4 individual concentrations are applied to the baths at a 4 min interval. After the end of the DRC and subsequent washing-out cycles (16 times in each case about 5 sec/min with the abovementioned nutrient solution), a 28-minute resting or incubation phase follows, within which the contractions as a rule reach the starting value again.

The height of the 3rd DRC, in a normal case, is used as a reference quantity for the assessment of the test substance to be investigated in further runs, which substance is applied to the baths in the following DRCs in increasing dose in each case at the start of the incubation period. Each aorta ring is in this case stimulated for the whole day, always with the same agonist.

Agonists and their standard concentrations (administration volume per individual dose=100 μl):

| | | |
|---|---|---|
| KCl | 22.7; 32.7; 42.7; 52.7 | mmol/l |
| l-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$; | g/ml |
| Methoxamine | $10^{-7}$; $10^{-6}$; $10^{-5}$; | g/ml |
| Angiotensin II | $3 \times 10^{-9}$; $10^{-8}$; $3 \times 10^{-8}$; $10^{-7}$ | g/ml |

To calculate the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

TABLE A

Inhibition of the vascular contraction in isolated rabbit aorta rings in vitro
$IC_{50}$ (g/ml) against contractions induced by AII

| Ex. No.: | $IC_{50}$ [nM] |
|---|---|
| 4 | 1400 |
| 9 | 920 |
| 13 | 240 |

Blood pressure measurements on the angiotensin II-infused rat

Male Wistar rats (Moellegaard, Copenhagen, Denmark) having a body weight of 300–350 g are anaesthetised with thiopental (100 mg/kg i.p.). After tracheotomy, a catheter for blood pressure measurements is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 μg/kg/min) is started. As soon as the blood pressure values have reached a stable plateau, the test substances are administered either intravenously or orally as a suspension or solution in 0.5% Tylose. The blood pressure changes under the action of substance are indicated as mean values±SEM in the table.

Determination of the antihypertensive activity in conscious hypertensive rats

The oral antihypertensive activity of the compounds according to the invention was tested in conscious rats having surgically induced unilateral renal artery stenosis. To do this, the right renal artery was constricted with a silver clip of 0.18 mm internal width. In this form of hypertension, the plasma renin activity is increased in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

The compounds according to the invention additionally inhibit the specific binding of radioactive angiotensin II in a concentration-dependent manner.

Interaction of the compounds according to the invention with the angiotensin II receptor in membrane fractions of the adrenal cortex (bovine)

Adrenal gland cortices from cattle (AGCs), which have been freshly removed and carefully freed from gland medulla, are comminuted in sucrose solution (0.32M) with the aid of an Ultra-Turrax (Janke & Kunkel, Staufen i.B.) to give a coarse membrane homogenate and partially purified to give membrane fractions in two centrifugation steps.

The receptor binding investigations are carried out on partially purified membrane fractions of bovine AGC using radioactive angiotensin II in an assay volume of 0.25 ml, which specifically contains the partially purified membranes (50–80 μg), $^3$H-angiotensin II (3–5 nM), test buffer solution (50 mM Tris, pH 7.2, 5 mM $MgCl_2$) and the substances to be investigated. After an incubation period of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The raw data were analysed using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

TABLE B

| Ex. No. | Ki [nM] |
|---|---|
| 9 | 120 |
| 13 | 72 |
| 16 | 440 |

Investigation of the inhibition of the proliferation of smooth muscle cells by the compounds according to the invention To determine the antiproliferative action of the compounds, smooth muscle cells are used which are obtained from aortas of pigs by the media explant technique [R. Ross, J. Cell. Biol. 50, 172, 1971]. The cells are inoculated into suitable culture dishes, as a rule 96-hole plates, and cultured at 37° C. in 5% $CO_2$ for 2–3 days in medium 199 containing 7.5% FCS and 7.5% NCS, 2 mmol L-glutamine and 15 mmol HEPES, pH 7.4. The cells are then synchronised for 2–3 days by withdrawal of serum and then stimulated into growth using serum or other factors. Test compounds are simultaneously added. After 16–20 hours, 1 μCi $^3$H-thymidine is added and after a further 4 hours the incorporation of this substance into the TCA-precipitatable DNA of the cells is determined.

To determine the $IC_{50}$ values, the active compound concentration is calculated which, on sequential dilution of the active compound, causes half-maximal inhibition of the thymidine incorporation produced by 1% FCS.

TABLE C

| Ex. No. | Inhibition [%] at $10^{-6}$ M |
|---|---|
| 6 | 41 |
| 7 | 100 |
| 10 | 12 |
| 11 | 100 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to reach the dosage range indicated.

The formulations are prepared, for example, by extending the active compounds using solvents and/or excipients, if appropriate using emulsifiers and/or dispersants, where, for example, in the case of the use of water as a diluent organic solvents can optionally be used as auxiliary solvents.

Administration is carried out in a customary manner, preferably orally or parenterally, in particular perlingually or intravenously.

In the case of parenteral administration, solutions of the active compound using suitable liquid excipient materials can be employed.

In general, it has proven advantageous in the case of intravenous administration to administer amounts from about 0,001 to 1 mg/kg, preferably about 0.01 to 0.5 mg/kg, of body weight to obtain effective results, and in the case of oral administration the dose is about 0.01 to 20 mg/kg, preferably about 0.1 to 10 mg/kg, of body weight.

In spite of this, it may sometimes be necessary to depart from the amounts mentioned, depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of the administration of larger amounts, it may be advisable to divide these into several individual doses over the course of the day.

TLC eluent mixtures
A=Dichloromethane: methanol=5:1
B=Dichloromethane: methanol=3:1
C=Dichloromethane: methanol=20:1
D=Dichloromethane: methanol=10:1
E=Petroleum ether: ethyl acetate=10:1
F=Petroleum ether: ethyl acetate=5:1
G=Dichloromethane: methanol=100:1
H=Petroleum ether: ethyl acetate=1:1

Starting Compounds

Example I trans-6-(4-Tolyl)-cyclohex-3-ene-1-carboxylic acid

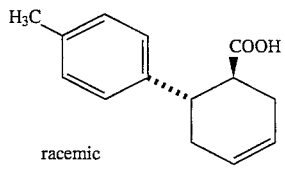

racemic 275 g (1.695 mol) of 3-(4-toluoyl)acrylic acid (commercially available from Aldrich) is reacted according to a known process [cf.: Eur. J. Med. Chem. 11, 493 (1976)] at about 200° C. and about 20 bar for 22 h with 580 ml of 1,3-butadiene (measured in condensed form) in 480 ml of toluene with the addition of 3 g of hydroquinone. The crude mixture is diluted with toluene and extracted with 0.5M aqueous sodium hydroxide solution. The aqueous phases are then acidified with 1M hydrochloric acid and extracted with ether. The ethereal solutions are dried with sodium sulphate, evaporated and redissolved in toluene. After boiling with 5 g of active carbon for 15 minutes, the mixture is filtered off hot with suction and the solvent is evaporated down to about 120–160 ml; at 0°–4° C. 124 g (573 mmol) of product crystallise out. The filtrate is concentrated somewhat further and cooled again for recrystallisation. On repeating this process altogether a further 42 g (194 mmol) of product are obtained.

$R_f$=0.39 (D)

Example II trans-2-(4-Tolyl)-cyclohexane-1-carboxylic acid

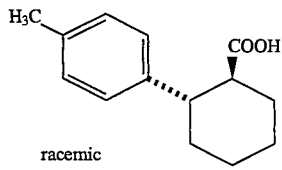

racemic 155 g (717 mmol) of the compound from Example I are dissolved in 1 l of methanol and the solution is reacted on 10 g of palladium (10% on animal charcoal) at 20° C. and a hydrogen atmosphere of about 1 bar. After a total reaction time of 16 h, the catalyst is filtered off and the solvent is evaporated—finally in a high vacuum.

Yield: 153 g (701 mmol) $R_f$=0.38 (D)

Example III (Method A)

tert-Butyl trans-2-(4-tolyl)-cyclohexane-1-carboxylate

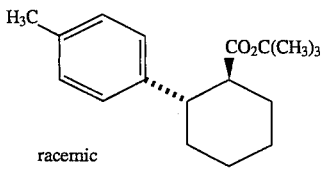

racemic 45.8 g (184 mmol) of the compound from Example II are dissolved in 600 ml of toluene and the solution is reacted under reflux with 49.5 ml (387 mmol) of oxalyl chloride. After 2 h, the solvent is evaporated with excess reagent; to do this, the crude carbonyl chloride must if necessary be taken up repeatedly in toluene and the solution evaporated once more in a rotary evaporator. The product thus obtained is dissolved in 500 ml of tetrahydrofuran, stirred at 0° C. with 24.8 g (221mmol) of potassium tert-butoxide and additionally stirred for 20 h (at 20° C.). Water and ether are then added and the mixture is extracted several times. The organic phase is dried using sodium sulphate and evaporated, and the residue is purified by chromatography on silica gel 60 (Merck, eluent mixture C).

Yield: 39.6 g (130 mmol) $R_f$=0.47 (E)

(Method B)

20.0 g (91.6 mmol) of the compound from Example II are suspended in 100 ml of ether with 7 ml of concentrated sulphuric acid and treated at −30° C. with 80 ml (713 mmol) of isobutene (pressure apparatus). The mixture is heated to 20° C. in the closed vessel and reacted over the course of 20 hours. It is then cooled again to −30° C., the apparatus is opened and the reaction mixture is stirred into 300 ml of 3M sodium hydroxide solution/400 ml of ether at 20° C. The aqueous phase is re-extracted with ether, and the organic solution is dried using sodium sulphate and evaporated.

Yield: 23.3 g (84.9 mmol).

Example IV tert-Butyl trans-2-(4-bromomethylphenyl)-cyclohexane-1-carboxylate

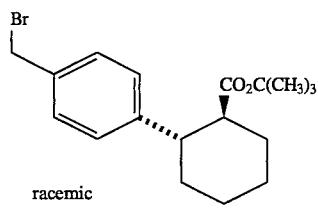

racemic 11.70 g (42.6 mmol) of the compound from Example III are reacted under reflux in 100 ml of tetrachloromethane with 7.59 g (42.6 mmol) of N-bromosuccinimide and 1.4 g of azobisisobutyronitrile. After a reaction time of 4 h, the mixture is cooled, the succinimide precipitate obtained is filtered off with suction and the filtrate is evaporated.

Yield: 14.2 g ( 40.2 mmol) $R_f$=0.48 (E)

Example V trans-2-(4-Tolyl)-cyclohexane-1-carbonitrile

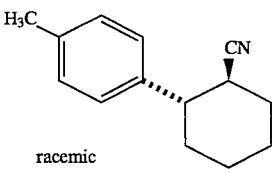

racemic 100.0 g (458.0 mmol) of the compound from Example II are reacted over the course of 1 hour at boiling heat in 1 l of dichloromethane with 84.3 g (595.5 g) of chlorosulphonyl isocyanate in 100 ml of dichloromethane. 72 ml (938.9 mmol) of N,N-dimethylformamide are then added dropwise to the cooling reaction mixture and it is stirred for 18 hours. It is poured onto 350 g of ice, the phases are separated after melting and the aqueous phase is extracted with dichloromethane. The organic phases dried using potassium carbonate are evaporated and the residue is distilled; 57.8 g (290.2 mmol) of product are obtained.

Boiling point: 122°–131° C. (0.2 mbar) $R_f$=0.81 (dichloromethane)

Example VI

5-[trans-2-(4-Tolyl)-cyclohex-1-yl]tetrazole

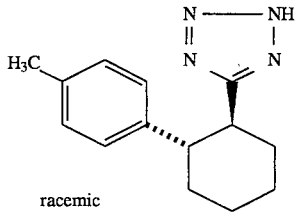

racemic 15.34 g (69.6 mmol) of the compound from Example V are reacted under nitrogen at boiling heat with 22.6 g (348 mmol) of sodium azide and 47.9 g (348 mmol) of triethylammonium chloride in 230 ml of anhydrous N,N-dimethylformamide; after 20 hours, the mixture is poured into ether and 1M sulphuric acid after cooling and then extracted with 10% strength sodium hydroxide solution. The aqueous phase is adjusted to pH=1.5 at 0° C. using 1M hydrochloric acid and the precipitate obtained is filtered off with suction, washed with water and dried in a high vacuum over phosphorus pentoxide and sodium hydroxide;

Yield: 11.2 g (46.2 mmol). $R_f$=0.23 (Dichloromethane: methanol=20:1)

Example VII

5-[trans-2-(4-Tolyl)-cyclohex-1-yl]-2-triphenylmethyltetrazole

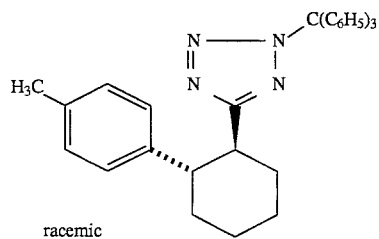

racemic 11.0 g (45.7 mmol) of the compound from Example VI are reacted at 0° C. with 13.4 g (48.2 mmol) of triphenylmethyl chloride and 7.57 ml (54.6 mmol) of triethylamine in 170 ml of dichloromethane. The mixture is stirred for about 20 h while warming to room temperature and then extracted with ether and aqueous citric acid. The organic phases are dried using sodium sulphate and evaporated;

Yield 22.1 g (45.5 mmol). $R_f$=0.67 (Petroleum ether: ethyl acetate=5:1)

Example VIII

5-[trans-2-(4-Bromomethylphenyl)-cyclohex-1-yl]-2-triphenylmethyl-tetrazole

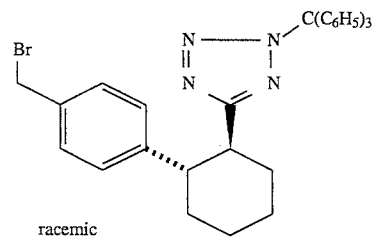

racemic 22.1 g (45.5 mmol) of the compound from Example VII are reacted under reflux with 8.1 g (45.5 mmol) of N-bromosuccinimide and 0.3 g of azobisisobutyronitrile in 300 ml of tetrachloromethane. After a reaction time of 3 hours, the mixture is cooled to room temperature and later to 0° C. and the precipitate is filtered off with suction. The filtrate is evaporated and a crude product (26.2 g) is obtained which is further reacted without further purification.

$R_f$=0.47 (Petroleum ether: ethyl acetate=10:1)

Preparation Examples

Example 1 tert-Butyl trans-2-[4-(2-butyl-4-chloro-5-formyl-imidazol-1-yl-methyl)phenyl]-cyclohexane-1-carboxylate

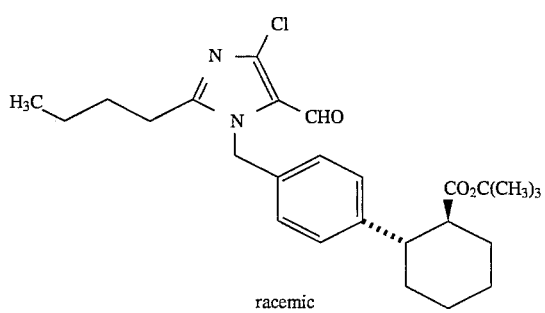

racemic 8.16 g (43.7mmol) of 2-butyl-4-chloro-5-formyl-imidazole [EP 324,377] are stirred with 1.32 g (43.7 mmol) of sodium hydride (80% strength, stabilised with paraffin) in 10 ml of dimethylformamide at about 0° C. until the evolution of hydrogen is complete. A solution of 18.4 g (43.7 mmol) of the compound from Example IV in 100 ml of dimethylformamide is then added dropwise and the mixture is stirred at 20° C. for 20 h. For working up, water is added and the mixture is extracted with ether. These organic phases are dried using sodium sulphate and concentrated in a rotary evaporator. The residue obtained is purified by chromatography on silica gel 60 (Merck, eluent E).

Yield: 7.81 g (17.0 mmol) $R_f$=0.67 (F)

Example 2 trans-2-[4-(2-Butyl-4-chloro-5-formyl-imidazol-1-yl-methyl)-phenyl]cyclohexane-1-carboxylic acid

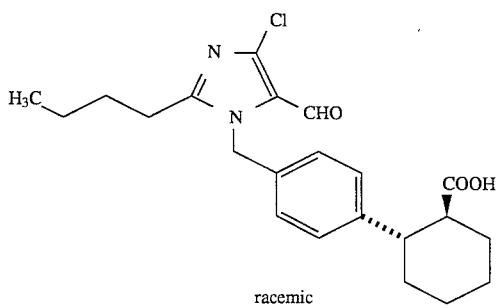

racemic 2.7 g (5.2 mmol) of the compound from Example 1 are reacted with 16 ml of concentrated hydrochloric acid in 40 ml of dioxane. After 18 h at 20° C., the mixture is diluted with ether, 1M aqueous sodium hydroxide solution is added and it is extracted by shaking. The aqueous alkaline phase (pH=13–14) is freed from residual organic solvent in vacuo and adjusted to pH=2 at 0° C. using 2M hydrochloric acid. The precipitate which deposits is filtered off with suction, washed with water and dried over sodium hydroxide and phosphorus pentoxide in a high vacuum.

Yield: 2.0 g (5.0 mmol) $R_f$=0.28 (C)

The compounds shown in Table 1 are prepared in analogy to the procedure of Example 2:

TABLE 1

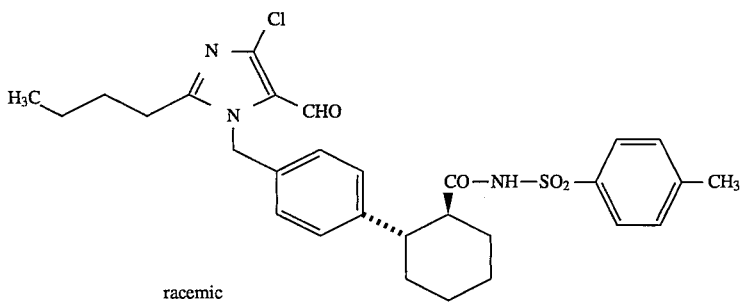

racemic

| Ex. No.: | D | $R_f$ (eluent) |
|---|---|---|
| 3 | $CH_2OH$ | 0.62 (A) |
| 4 | COOH | 0.21 (B) |

Example 5

N-(4-Tolylsulphonyl)trans-2-[4-(2-butyl-4-chloro-5 -formyl-imidazole-1-yl-methyl)phenyl]cyclohexane-1-carboxamide racemic 0.7 g (1.5 mmol) of the compound from Example 2 are reacted at −20° C. with 0,127 ml (1.65 mmol) of methanesulphonyl chloride and 0.91 ml (6.6 mmol) of triethylamine in 30 ml of tetrahydrofuran; after 2 h at this temperature 0.73 g (6.0 mmol) of 4-(N,N-dimethylamino)pyridine and 0.31 g (1.8 mmol) of 4-toluenesulphonamide are added and the reaction mixture is stirred at 20° C. for 24 h. It is then poured into 1M hydrochloric acid and extracted several times with ether. The organic phases are dried using sodium sulphate and evaporated, and the residue obtained is purified by chromatography on silica gel 60 (Merck: eluent G).

Yield: 0.72 g (1.3 mmol) $R_f$=0.72 (C)

Example 6 and Example 7

(S)-phenylglycinol-[1,2-trans]-2-[4-(2-butyl-4-chloro-5 -formyl-imidazol-1-yl-methyl)-phenyl]-cyclohexane-1-carboxamide

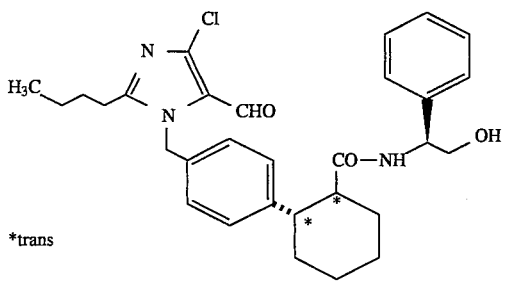

*trans 1.3 g (2.8 mmol) of the compound from Example 2 are reacted at −30° C. with 0.78 ml (5.6 mmol) of triethylamine and 0.235 ml (3.1 mmol) of methanesulphonyl chloride in 30 ml of tetrahydrofuran. After 30 minutes at −30° C., a solution of 459 mg (3.3 mmol) of (S)-phenylglycinol and 0.34 g (2.8 mmol) of 4-(N,N-dimethylamino)pyridine in 10 ml of tetrahydrofuran is added dropwise and the mixture is stirred for 24 h while warming to 20° C. It is poured into 1M hydrochloric acid and extracted several times with ether. The organic phases are dried using sodium sulphate and evaporated, and the residue is resolved by chromatography (silica gel 60, Merck)

Yield: 186 mg (0.36 mmol) of Example 6 (Diastereomer A) 591 mg of Example 6/7 (Diastereomer mixture A+B) 230 mg (0.44 mmol) of Example 7 (Diastereomer B) $R_f$=0.32 (H) Example 6 $R_f$=0.17 (H) Example 7

Example 8 tert-Butyl trans-2-[4-(2-butyl-4-chloro-5-hydroxymethylimidazol-1-yl-methyl)phenyl]-cyclohexane-1-carboxylate

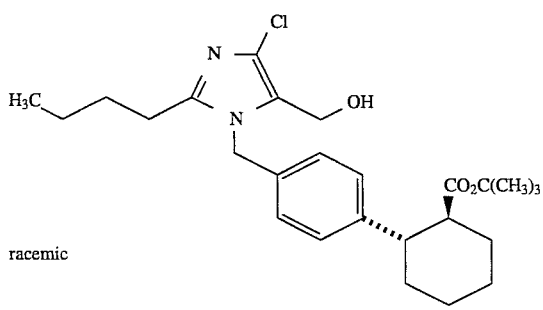

racemic 1 g (1.9 mmol) of the compound from Example 1 is dissolved in 10 ml of ethanol and reacted at 20° C. with 74.2 mg (2.0 mmol) of sodium borohydride. After 1 h, water is added and the mixture is extracted with ether.

The organic phase is dried using sodium sulphate and evaporated.

Yield: 0.97 g (1.85 mmol) $R_f$=0.53 (H)

The compounds shown in Table 2 are prepared analogously to Example 8:

TABLE 2

| Ex. No. | $R^7$ | $R_f$ (eluent) |
|---|---|---|
| 9 | —SO$_2$—C$_6$H$_4$—CH$_3$ | 0.27 (C) |
| 10 | —CH(CH$_3$)CH$_2$OH (phenyl) | 0.38 (C) Diastereomer A |
| 11 | —CH(CH$_3$)CH$_2$OH (phenyl) | 0.32 (C) Diastereomer B |

\* trans

Example 12 tert-Butyl trans-2-[4-(2-butyl-4-chloro-5-carboxyimidazol-1-yl-methyl)phenyl]-cyclohexane-1-carboxylate

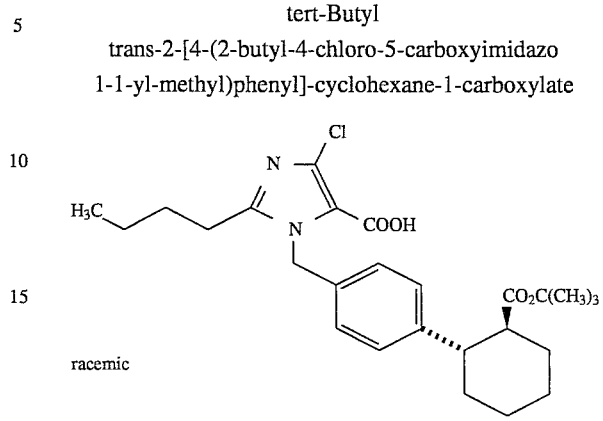

racemic 1.0 g (1.9 mmol) of the compound from Example I are dissolved in 9 ml of tert-butanol and reacted at 20° C. with 7.7 ml of 1.25M aqueous sodium dihydrogen phosphate solution and 11.5 ml of 1M aqueous potassium permanganate solution. After 10 minutes, the reaction is stopped by addition of saturated, aqueous sodium sulphite solution, adjusted to pH=3.5 with 1M hydrochloric acid and extracted with ethyl acetate. After evaporation of the solvent, the residue is taken up in ether and the mixture is extracted with 2M aqueous sodium hydroxide solution. The aqueous phase is freed from residual solvent in vacuo and adjusted to pH=1 at 0° C. with 1M hydrochloric acid, and the precipitate obtained is filtered off with suction, washed with water and dried over sodium hydroxide and phosphorus pentoxide in a high vacuum.

Yield: 120 mg (0.2 mmol) $R_f$=0.28 (D)

After extraction with sodium hydroxide solution, the ethereal phase contains 81% of the starting material.

Example 13

N-(4-Tolylsulphonyl)-trans-2-[4-(2-butyl-4-chloro-5-carboxy-imidazol-1-yl-methyl)phenyl]-cyclohexane-1-carboxamide

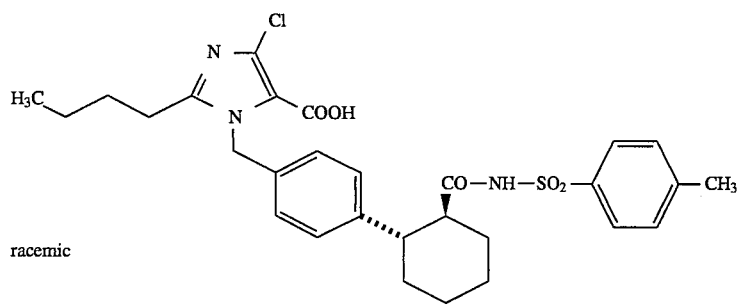

racemic

The title compound is prepared in analogy to the procedure of Example 12.

$R_f$=0.11 (c)

Example 14

5-[trans-2-(4-{2-Butyl-4-chloro-5-formyl-imidazol-1-yl-methyl}phenyl)-cyclohex-1-yl]-2-triphenylmethyl-tetrazole The title compound is prepared in analogy to Example 1:

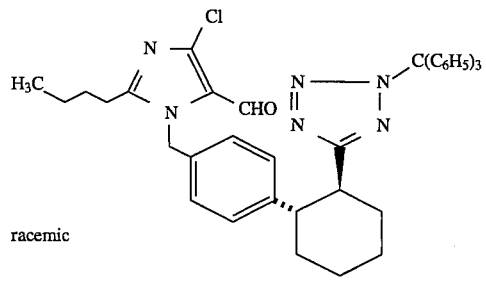

racemic $R_f$=0.72 (Petroleum ether: ethyl acetate=2:1)

Example 15

5-[trans-2-(4-{2-Butyl-4-chloro-5-hydroxymethyl-imidazol-1-yl-methyl}-phenyl)-cyclohex-1-yl]-2-triphenylmethyl-tetrazole The title compound is prepared in analogy to Example 8:

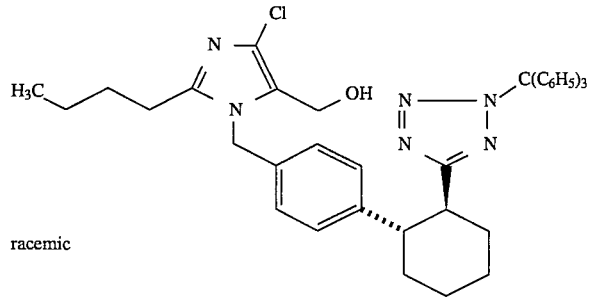

racemic $R_f$=0.23 (Petroleum ether: ethyl acetate=2:1)

Example 16

5-{trans-2-[4-(2-Butyl-4-chloro-5-formyl-imidazol-1-yl-methyl)-phenyl]-cyclohex-1-yl}-tetrazole

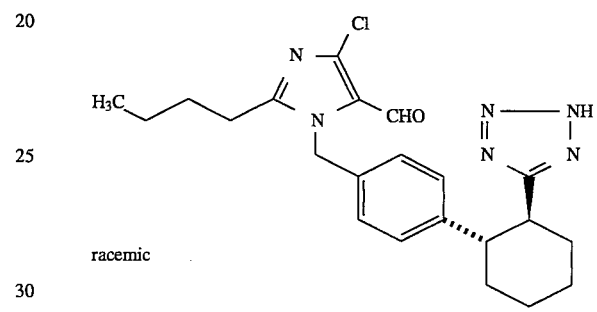

racemic 0.2 g (0.3 mmol) of the compound from Example 14 are reacted with 1 ml of water and 1 ml of trifluoroacetic acid in 2 ml of tetrahydrofuran. After 2 hours at room temperature, the mixture is poured onto ether/water and adjusted to pH=13 with 10% strength sodium hydroxide solution. The aqueous phase is adjusted to pH = 2 at 0° C. using 1M hydrochloric acid, and the product precipitates. Filtering off with suction and drying over phosphorus pentoxide and sodium hydroxide in a high vacuum yield 0.1 g (0.2 mmol).

$R_f$=0.10 (Dichloromethane: methanol=50:1)

Example 17

5-{trans-2-(4-[2-Butyl-4-chloro-5-hydroxymethyl-imidazol-1-yl-methyl)-phenyl]-cyclohex-1-yl}-tetrazole The title compound is prepared in analogy to the procedure of Example 16:

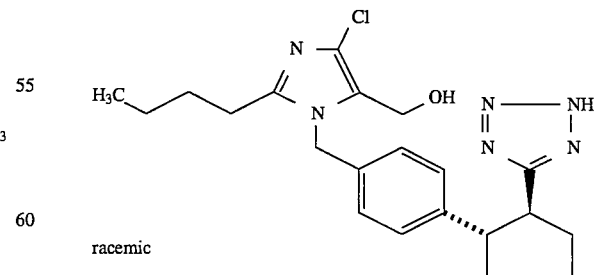

racemic $R_f$=0.41 (Dichloromethane: methanol=10:1)

We claim:

1. An imidazolyl-substituted cyclohexane of the formula

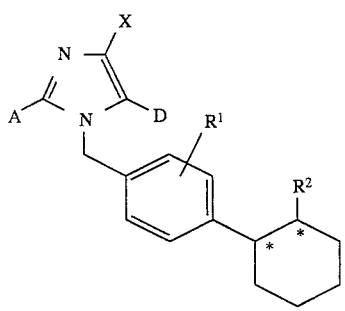

in which

A is alkyl or alkenyl each having up to 8 carbon atoms, or is cycloalkyl having 3 to 8 carbon atoms, X is hydrogen, halogen or perfluoroalkyl having up to 5 carbon atoms, D is —CH$_2$—OR$^3$ or —CO—R$^4$, in which R$^3$ is hydrogen or alkyl having up to 8 carbon atoms, R$^4$ is hydrogen, hydroxyl or alkoxy having up to 8 carbon atoms, R$^1$ is hydrogen, halogen, nitro, hydroxyl, trifluoromethyl, trifluoromethoxy, alkyl, alkoxy or alkoxycarbonyl each having up to 6 carbon atoms, cyano or carboxyl, and R$^2$ is —CO—NR$^6$R$^7$, in which R$^6$ is hydrogen or alkyl having up to 6 carbon atoms, R$^7$ is —SO$_2$R$^9$ or

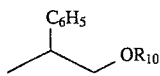

in which

R$^9$ is alkyl having up to 8 carbon atoms, which is optionally substituted by phenyl or tolyl, or is phenyl which is optionally substituted by halogen or by alkyl having up to 6 carbon atoms, and R$^{10}$ is hydrogen, alkyl having up to 6 carbon atoms or a hydroxyl protective group, wherein said group is selected from the group consisting of triethylsilyl, triisopropylsilyl, tert-butyldimethylsilyl, tert-butyldiphenylsilyl, trimethylsilylethoxycarbonyl, benzyl, triphenylmethyl (trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butoxycarbonyl, 4-methoxybenzyl, 4-methoxybenzyloxycarbonyl, formyl, acetyl, trichloroacetyl, 2,2,9-trichloroethoxycarbonyl, 2,4-dimethoxybenzyl, 2,4-dimethoxybenzyloxycarbonyl, methoxymethyl, methylthiomethyl, methoxyethoxymethyl, [2- (trimethylsilyl)ethoxy]methyl, 2 -(methylthiomethoxy)-tetrahydropyranyl, benzoyl, ethoxycarbonyl, 4-nitrobenzoyl, 4-fluorobenzoyl, 4 -methylbenzoyl, 4-chlorobenzoyl, or 4-methoxybenzoyl, or a salt thereof.

2. An imidazolyl-substituted cyclohexane or salt thereof according to claim 1,

A is alkyl or alkenyl each having up to 6 carbon atoms, or is cyclopropyl, cyclobutyl, cyclopentyl, cyclohexyl or cycloheptyl, X is hydrogen, fluorine, chlorine, bromine or perfluoroalkyl having up to 4 carbon atoms, D is —CH$_2$OR$^3$ or —CO—R$^4$, in which R$^3$ is hydrogen or alkyl having up to 6 carbon atoms, R$^4$ is hydrogen, hydroxyl or alkoxy having up to 6 carbon atoms, R$^1$ is hydrogen, fluorine, chlorine, bromine, trifluoromethyl, carboxyl or alkyl, alkoxy or alkoxycarbonyl each having up to 4 carbon atoms, R$^2$ is —CO—NR$^6$R$^7$, in which R$^6$ is hydrogen or alkyl having up to 4 carbon atoms, and R$^8$ is —SO$_2$—R$^9$ or

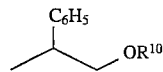

in which

R$^9$ is alkyl having up to 6 carbon atoms, which is optionally substituted by phenyl or tolyl, or is phenyl which is optionally substituted by fluorine, chlorine or bromine, or by alkyl having up to 4 carbon atoms, and R$^{10}$ is hydrogen or alkyl having up to 4 carbon atoms or benzyl.

3. An imidazolyl-substituted cyclohexane or salt thereof according to claim 1, in which A is alkyl or alkenyl each having up to 4 carbon atoms, or is cyclopropyl, cyclopentyl or cyclohexyl, X is hydrogen, fluorine, chlorine or perfluoroalkyl having up to 3 carbon atoms, D is —CH$_2$OR$^3$ or —CO—R$^4$, in which R$^3$ denotes hydrogen or alkyl having up to 4 carbon atoms, R$^4$ is hydrogen, hydroxyl or alkoxy having up to 4 carbon atoms, R$^1$ is hydrogen, fluorine, chlorine, bromine, trifluoromethyl or methyl, R$^2$ is —CO—NR$^6$R$^7$, in which R$^6$ is hydrogen, methyl or ethyl, R$^7$ is —SO$_2$R$^9$ or 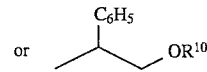

in which

R$^9$ is alkyl having up to 4 carbon atoms, which is optionally substituted by phenyl or tolyl, or is phenyl or tolyl, and R$^{10}$ is hydrogen, methyl or ethyl.

4. A compound according to claim 1 wherein such compound is N-(4 -tolylsulphonyl)-trans-2-[4-(2-butyl-4-chloro-5-formyl-imidazole-1 -yl-methyl)-phenyl]cyclohexane-1-carboxamide of the formula

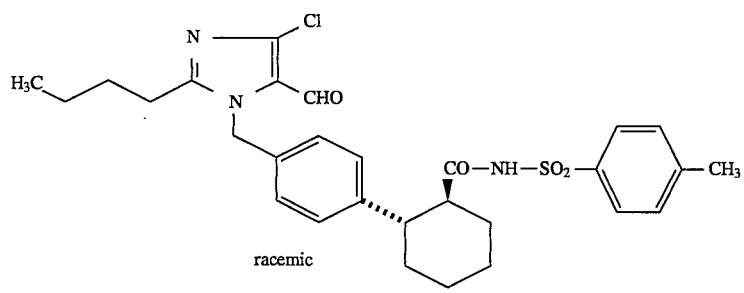

racemic or a salt thereof.

5. A composition for the treatment of arterial hypertension and atherosclerosis comprising an amount effective therefor of a compound or salt thereof according to claim 1 and a pharmacologically acceptable diluent.

6. The method of treating arterial hypertension and atherosclerosis in a patient in need thereof which comprises adminstering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,508,299
DATED : April 16, 1996
INVENTOR(S) : Muller, et al.

It is certified that error appears in the above-indentified patent and that said Letters Patent is hereby corrected as shown below:

| | |
|---|---|
| Col. 25, line 52 | Delete " 2,2,9-trichloroethoxy- " and substitute -- 2,2,2-trichloroethoxy- -- |
| Col. 25, line 56 | After " 2-(methylthiomethoxy)- " insert -- ethoxycarbonyl, -- |
| Col. 25, line 57 | Delete " ethoxycarbonyl, " and substitute -- 4-methylbenzoyl -- |
| Col. 25, line 58 | Delete " 4-methylbenzoyl, " |

Signed and Sealed this

Twenty-seventh Day of August, 1996

Attest:

BRUCE LEHMAN

Attesting Officer        Commissioner of Patents and Trademarks